United States Patent [19]

Shiu et al.

[11] Patent Number: 5,487,394
[45] Date of Patent: Jan. 30, 1996

[54] TUNGSTEN EYE SHIELDS FOR ELECTRON BEAM TREATMENT

[75] Inventors: Almon S. Shiu, Bellaire; Samuel S. Tung, Missouri City; Robert J. Gastorf, Houston, all of Tex.

[73] Assignee: The Board of Regents of the University of Texas System, Austin, Tex.

[21] Appl. No.: 278,757

[22] Filed: Jul. 22, 1994

[51] Int. Cl.⁶ .................................. A61F 5/37; A61F 9/00
[52] U.S. Cl. .................. 128/846; 128/858; 2/15
[58] Field of Search ..................... 128/857, 858, 128/846; 2/426, 432, 431, 433, 434, 439, 454, 15

[56] References Cited

U.S. PATENT DOCUMENTS

| | | |
|---|---|---|
| 2,379,629 | 7/1945 | Eweson . |
| 2,415,384 | 2/1947 | Bushnell . |
| 3,619,815 | 11/1971 | Towner .................... 128/858 |
| 3,973,561 | 8/1976 | Kane . |
| 4,122,847 | 10/1978 | Craig . |
| 4,406,285 | 9/1983 | Villasenor et al. . |
| 4,570,626 | 2/1986 | Norris ...................... 128/858 |
| 4,937,879 | 7/1990 | Hall ............................ 2/8 |
| 4,990,150 | 2/1991 | Tsubota et al. . |
| 5,021,057 | 6/1991 | Byrne, Jr. . |
| 5,140,710 | 8/1992 | Rademacher ................. 2/432 |
| 5,191,897 | 3/1993 | Meshel ..................... 128/858 |
| 5,309,925 | 5/1994 | Policastro ................. 128/849 |

FOREIGN PATENT DOCUMENTS 9319707  10/1993  WIPO ...................... 128/858

OTHER PUBLICATIONS

Medical Physics 20:891, Jun. 1993; "*Abstract*", Almon S. Shiu, Smauel S. Tung; Robert J. Gastorf; Kenneth R. Hogstrom; William H. Morrison, and Lester J. Peters.
British Journal of Radiology, 47:467–470, Aug. 1974; "*Back-scattering from Metals in Superficial Therapy with High energy Electrons*" by J. E. Saunders; V. G. Peters.
British Journal of Radiology, 53:466–470, 1980; "*Dose Enhancement from Backscattered Radiation at Tissue-metal Interfaces Irradiated with High Energy Electrons*" by W. F. Gagnon; J. H. Cundiff.
Phys. Med. Biol, vol. 27, No. 3, 363–373, 1982; "*Backscattering in Electron Beam Therapy for Energies between 3 and 35 MeV*" by S. C. Klevenhagen; G. D. Lambert; A. Arbabi.

*Primary Examiner*—Michael A. Brown
*Attorney, Agent, or Firm*—Rosenblatt & Redano

[57] ABSTRACT

An eye shield for use in electron beam treatment of eyelid tumors. The use of tungsten provides an eye shield which is sufficiently thin to allow insertion over the eye and underneath the eyelid while providing sufficient shielding to protect against ocular damage when electron beams of up to nine million electron volts are used. A coating applied to the outer surface of the shield prevents burning of the tissues at the eyelid-shield interface resulting from backscattered electrons.

16 Claims, 1 Drawing Sheet

TUNGSTEN EYE SHIELDS FOR ELECTRON BEAM TREATMENT

BACKGROUND OF THE INVENTION

1. Field of the Invention

This invention relates to an eye shield to protect ocular structures during electron beam treatment of eyelid tumors.

2. Description of the Prior Art

Protection of the ocular structures of the eye is important in eye surgery and treatments of tissue surrounding the eye. The goal in such procedures is usually both the correction of a medical problem and the preservation of ocular function. Eye shields and related devices have been designed for use in various procedures to meet these goals. Each shield or device was designed to avoid hazards particular to the procedure for which the shield was to be used.

U.S. Pat. No. 4,570,626 to Norris and Schwartz discloses an opaque shield which is of smaller diameter than the cornea. This shield is intended to prevent damage to the retina from bright lights used during optical surgery, for example, during the removal of cataracts. This shield may be constructed of various materials, such as rigid or flexible plastics. Its primary qualities are that it is opaque to visible light and that it is smaller than the cornea.

U.S. Pat. No. 5,021,057 to Byrne discloses a tool for use in closing anterior segment openings and preventing hemorrhages. This tool is characterized by its transparency, allowing the surgeon to visually monitor the eye, and by an opening which allows the surgeon to suture the area underneath the tool.

U.S. Pat. No. 4,990,150 to Tsubota and Sakai discloses a bandage to hold an incision closed without the need for a temporary suture. This bandage is useful during invasive, and especially during protracted, surgical procedures to protect the integrity of the anterior chamber of the eye.

U.S. Pat. No. 4,406,285 to Villasenor and Krasnow discloses a template for use in performing radial keratotomy. The template is shaped to fit over the cornea and provides slits to guide a surgical blade. The slits are designed to provide precise location for the incisions and to regulate the depth of the incisions.

U.S. Pat. No. 4,122,847 to Craig discloses a flexible mask which covers the eyes and a portion of the surrounding skin. The mask is designed for use in surgery to prevent extraneous fluids from being introduced into the patient's eyes. The portion of the mask which covers the eyes is transparent to allow observation of eye condition, for example, by an anesthesiologist.

U.S. Pat. No. 3,973,561 to Kane discloses an eye covering to protect the eyes of large domestic animals in the case of disease or infection. The shield is designed to cover the entire eye and is opaque. It is further designed of a flexible material so it can return to its original shape if deflected.

U.S. Pat. No. 2,415,384 to Bushnell discloses an eye cover for people who have lost an eye. It is designed to cover the entire eye socket and has a base extending into the eye socket for anchoring. The preferred material is thermoplastic or a noncorrosive and nonirritating metal.

U.S. Pat. No. 2,379,629 to Eweson discloses a piston device with a suction cup on the end for use in inserting and removing contact lenses.

Internal eye shields designed for shielding during orthovoltage X-ray treatments are commercially available. Internal, plastic-coated lead eye shields are commercially available from Ace Medical Supply Co., 799 Broadway, New York, N.Y. 10003. Such shields have also been made with a gold coating, although this coating is unstable and may irritate the patient's cornea during treatment.

The foregoing devices solve particular problems associated with certain procedures for eye surgery or other treatment of eye problems. However, they do not provide a solution for the problem of protecting the ocular structures from damage during high energy electron beam treatment of eyelid tumors. None of the patented devices is designed for insertion between the eyelid and the surface of the eye, as is necessary to protect against electrons which are transmitted through the eyelid's tissue. The materials used in the patented shields are selected for transparency or opacity to visible light rather than high energy electrons. Additionally, an eye shield for use during electron beam treatment of eyelid tumors must avoid backscattering of electrons which could burn tissues by increasing the total dosage above clinically acceptable limits. Finally, the commercially available internal shields do not provide sufficient shielding to protect against ocular damage during the use of high energy electron beams.

SUMMARY OF THE INVENTION

It is an object of this invention to provided an eye shield for use during electron beam treatment of eyelid tumors which protects the eye from damage and is sufficiently thin to be inserted underneath the eyelid.

It is another object to provide such protection while using electron beam energies of up to nine million electron volts.

It is another object to provide such protection with an eye shield of less than three millimeters thickness.

It is a further object to provide an eye shield which avoids damage to the tissue immediately adjacent to the outer surface of the shield which could result from the backscattering of electrons.

It is another object to provide an eye shield which can he easily manipulated for both insertion and removal over the eye.

It is another object to provide an eye shield which is easily sterilizable and which does not promote the growth of bacteria on its surface.

To achieve these and other objectives, an eye shield is provided having a tungsten body of sufficient thickness to protect the eye from electron beam damage. The shield has a curved inner surface and a curved outer surface. In use, the inner surface of the shield will be in contact with or close to the cornea. The outer surface of the shield will be in contact with the inner surface of the eyelid and may be partially exposed to the open air. The surfaces are curved to allow a good fit to the curvature of the eye and eyelid.

To protect the eye from damage, the body must be sufficiently thick to attenuate electron beams in the energy range of six to nine million electron volts so that the tolerance doses to different optic structures within the eye are not exceeded. A tolerance dose is the maximum dose of electrons of a particular energy which can be incident on an optic structure without causing unacceptable damage to the optic structure. It is preferred that the shield also cover a surface area large enough to shield all optic structures of the eye during electron beam bombardment.

To accomplish these goals, the shield should reduce the electron dose at the inner surface to no more than ten percent, and preferably to no more than five percent, of the electron dose at the outer surface of the shield. The electron dose at the outer surface of the shield is also referred to as the open field dose.

The shield's reduction of the open field dose is dependent on the electron beam energy, the shield thickness, and the shield material. As beam energy increases, the amount of required shielding also increases. For treatment of eyelid tumors, electron beam energies of up to nine million electron volts (9 MeV) are used. Accordingly, the shield must be capable of attenuating 9 MeV electrons so that the dose at the cornea is no more than ten percent of the open field dose.

The shield thickness is the perpendicular distance between the inner surface and the outer surface. For this application, it is important that the body is sufficiently thin so that the shield can be inserted between an eye and an eyelid. Preferably, the shield thickness should not exceed three millimeters. To achieve the needed reduction of the open field dose by a shield of no more than 3 mm thickness, tungsten was chosen as the material for the shield body. Other materials, such as lead, were rejected because the thickness needed to obtain sufficient shielding makes the shield too thick to be practical. For example, it was experimentally verified that a lead shield would have to be 4.5 mm thick to provide sufficient protection from a 9 MeV electron beam. By contrast, a tungsten shield of 2.5 mm thickness was constructed and shown to attenuate an 8.7 MeV electron beam so that the dose at the cornea is no more than five percent of the open field dose.

Another problem encountered with the use of metal shields in electron beam treatment is backscattering of electrons. As electrons are backscattered, they can increase the electron dose on tissues. In this application, the backscattered electrons may strike the inner surface of the eyelid where it is in contact with the outer surface of the eye shield. These backscattered electrons were found to increase the effective dose at the inner surface of the eyelid to approximately 140 percent of the open field dose. This backscattering problem may be reduced by applying a 2 mm coating of material to the outer surface of the tungsten body of the eye shield. The material should be one which is capable of reducing electron backscattering. A preferred material to use for this coating is dental acrylic.

It is also desirable to provide an extension to the outer surface of the eye shield by which the shield may be grasped and lifted. This extension allows the shield to be easily moved and inserted on or removed from the eye. A preferred means of forming such an extension is to machine or mold the eye shield with an integral member perpendicular to the outer surface of the shield and extending away from the shield.

Further objects and features of the invention will be apparent to those skilled in the art from the following detailed description of preferred embodiments, taken together with the accompanying drawing.

DETAILED DESCRIPTION OF THE PREFERRED EMBODIMENTS

Figure 1:
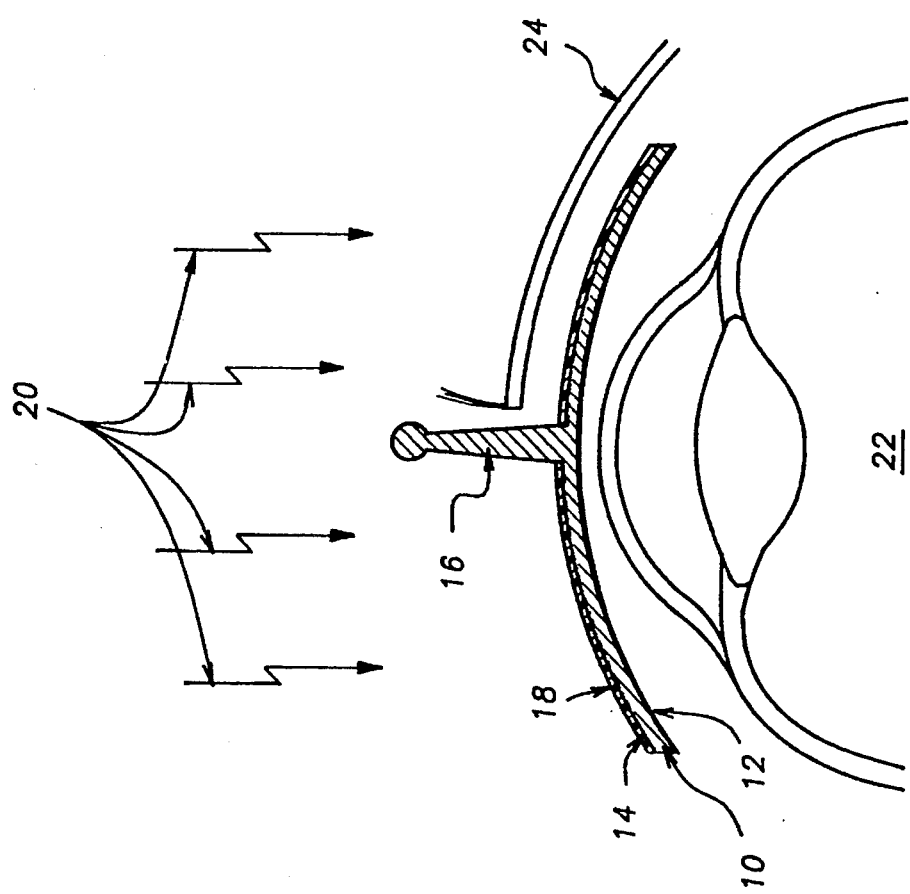
FIG. 1 is a side elevational view of one embodiment of the eye shield.

Referring to FIG. 1, the eye shield is comprised of a tungsten body 10 having an inner surface 12 and an outer surface 14. The shield is placed over the eye 22 and beneath the eyelid 24. High energy (up to about 9 MeV) electrons 20 bombard the eyelid 24 and outer surface of the shield 14. In a preferred embodiment, an extension 16 is attached to the outer surface, allowing the shield to be grasped and lifted by the extension. Another preferred feature is a thin coating of dental acrylic 18 applied to the outer surface of the body 10 to reduce the backscattering of electrons from the body.

Many modifications and variations may be made in the embodiments described herein and depicted in the accompanying drawing without departing from the concept of the present invention. Accordingly, it is understood that the embodiments described and illustrated herein are illustrative only and are not intended as a limitation upon the scope of this invention.

What is claimed is:

1. An eye shield for insertion between an eye and an eyelid, comprising a tungsten body having a curved inner surface and a curved outer surface, the body being sufficiently thick to attenuate electron beams in the energy range of six to nine million electron volts such that the tolerance doses to different optic structures within an eye are not exceeded and the body being sufficiently thin such that the shield can be inserted between an eye and an eyelid.

2. The eye shield of claim 1 wherein the shield is no more than 3.0 millimeters thick.

3. The eye shield of claim 1 wherein the shield is no more than 2.5 millimeters thick.

4. The eye shield of claim 1 wherein the shield is sufficiently thick so that, when the outer surface of the shield is subjected to a beam of electrons with energies up to about nine million electron volts, the electron dose at the inner surface of the shield is less than ten percent of the electron dose at the outer surface.

5. The eye shield of claim 1 wherein the shield is sufficiently thick so that, when the outer surface of the shield is subjected a beam of electrons with energies up to about nine million electron volts, the electron dose at the inner surface of the shield is less than five percent of the electron dose at the outer surface.

6. The eye shield of claim 1 wherein the outer surface also comprises an extension by which the shield can be grasped and lifted.

7. The eye shield of claim 1, wherein the surface area covered by the shield is sufficiently large to shield all optic structures of an eye during electron beam bombardment.

8. The eye shield of claim 1, wherein the outer surface is coated with a material capable of reducing a portion of electron backscattering.

9. The eye shield of claim 8, wherein the coating material is a dental acrylic.

10. An eye shield for insertion between an eye and an eyelid, comprising a tungsten body having a curved inner surface and a curved outer surface, the body being sufficiently thick to attenuate electron beams in the energy range of six to nine million electron volts such that the tolerance doses to different optic structures within the eye are not exceeded and the body being sufficiently thin such that the shield can be inserted between an eye and an eyelid, and where the outer surface also comprises a coating over the tungsten body so that the electron backscatter rate is reduced.

11. The eye shield of claim 10 wherein the coating on the outer surface is a dental acrylic.

12. The eye shield of claim 10 wherein the shield is no more than 3.0 millimeters thick.

13. The eye shield of claim 10 wherein the shield is no more than 2.5 millimeters thick.

14. The eye shield of claim 10 wherein the shield is sufficiently thick so that, when the outer surface of the shield is subjected a beam of electrons with energies up to about nine million electron volts, the electron dose at the inner surface of the shield is less than ten percent of the electron dose at the outer surface.

15. The eye shield of claim 10 wherein the shield is sufficiently thick so that, when the outer surface of the shield is subjected a beam of electrons with energies up to about nine million electron volts, the electron dose at the inner surface of the shield is less than five percent of the electron dose at the outer surface.

16. The eye shield of claim 10 wherein the outer surface also comprises an extension by which the shield can be grasped and lifted.

* * * * *